May 13, 1958 O. R. BRISTOW Plant Pat. 1,708
AZALEA PLANT
Filed July 30, 1957
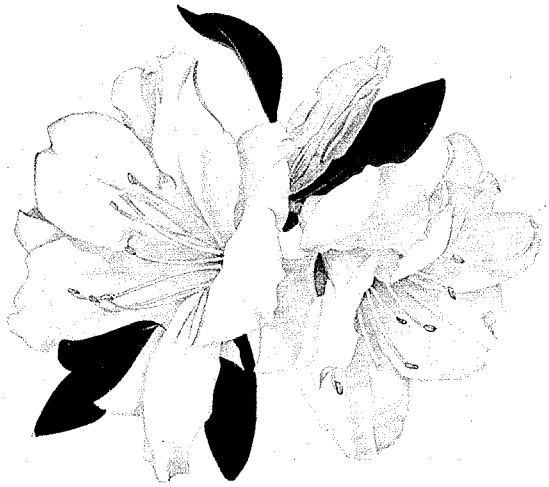
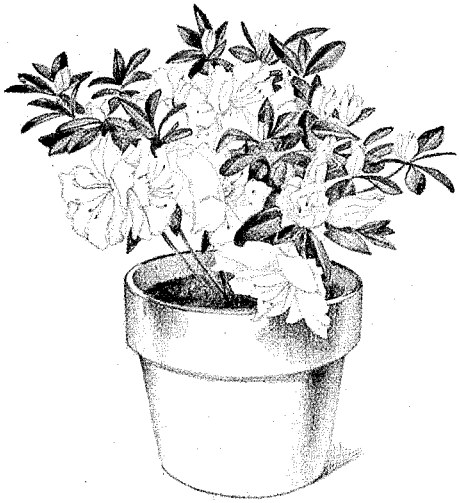
OWEN R. BRISTOW
INVENTOR.
BY Orville R. Seidney
AGENT United States Patent Office Plant Pat. 1,708
Patented May 13, 1958

1,708

AZALEA PLANT

Owen R. Bristow, San Bernardino, Calif., assignor to Mossholder Nursery, Orange County, Calif.

Application July 30, 1957, Serial No. 675,238

1 Claim. (Cl. 47—60)

This invention relates to a distinct and new variety of white azalea plant reproduced as a result of deliberate experiments in hybridization carried out at my nursery in San Bernardino, California, the plant being derived from a cross-breeding of unpatented plants numbered 109B and 42 in my breeding records. This particular plant has been given the number 13WW for identification purposes.

The cross-breeding resulting in plant 13WW was accomplished as follows: cross-fertilization of the pistils by pollen of plants 109B and 42 was done, after which the resulting seed pods on the two plants were gathered and all seeds subsequently sown at the same time. The seeds from the pods of the two plants were inadvertently mingled, hence the sex parentage as between plants 109B and 42 is unknown for the present plant 13WW. It will be noted that both plants 109B and 42 were used as males and females and pods from both of them were gathered and sown, the present plant 13WW being a seedling result of the sowing. Seedling plant 13WW was thereafter transplanted at my nursery in San Bernardino, California, were asexual reproduction by the known method of removing cuttings from the mature plant and potting them was accomplished by me.

This distinct and new variety of white azalea is characterized by several particularly distinguishing features. The plant itself is a good grower which matures into a compact plant when properly pinched. It is a good consistent setter of greenish-yellow buds which tend to diminish in color saturation as they develop into the opening flowers, notwithstanding that the greenish-yellow color deepens at the base of the buds.

An exceptional characteristic is that the plant is an unusually late bloomer which will not force early in the blooming season but can be forced for a late April Easter or Mother's Day, hence has valuable commercial features as a forcing white.

The plant is also characterized by slightly smaller than average foliage. The flower is a trumpet-shaped hose-in-hose with prominent stamens.

Asexual reproduction by cuttings of this distinct and new variety of azalea indicates the foregoing characteristics, as well as further distinguishing characteristics brought forth in the description below, are permanently fixed, and the accompanying illustration of a forced cutting plant in bloom shows the plant, foliage, and flower as near as may be represented.

The following is a detailed specification of the plant, its foliage, and the flower.

*Plant*

Form of plant: Bushy, compact, symmetrical. When not properly pinched or pruned, young plants will tend to grow more tall than wide.
Growth habit: A fast grower.
Rooting: Roots well; strong grower on its own roots.

Blooming habit: Prolific; usually 3 buds on each stem, occasionally 2 and rarely 4.
Blooming season: Later than most all other related azaleas; late April or early May.
Suitability for forcing: Good for a late forcer.

*Foliage*

Size: Mature leaves average 5/8" wide by 1¾" in length.
Quantity: Average.
Color: New foliage—light green, semi-glossy on upper side; light green flat on under side. Old foliage—dark green, glossy on upper side; light green, semi-glossy on under side.
Shape: Oval; slightly pointed.
Texture: Normal.
Edge or margin: Normal.
Ribs and veins: Average.
Aspect: Leaves are smaller than average related azaleas; otherwise normal.

*Flower*

Size: 3" across flower is average. Occasionally, flowers are 2" to 2½" across.
Flowers borne: 3 on each stem; occasionally only 2, rarely 4.
Quantity of bloom: Abundant.
Continuity: Flowers hold exceptionally well.
Petalage:
Size.—7/8" wide, 2" long.
*Number of petals under normal conditions.*—5 on inside hose or cycle of petals: 5 on outside hose or cycle of petals.
*Color of buds.*—First showing ivory-white on end of bud shading to greenish-yellow towards the base of bud; as the bud develops toward the opening flower, the intensity of the greenish-yellow color diminishes.
*Color of open flower.*—When the flower first opens, it is white toward the ends of the petals; gradually it becomes slightly greenish-yellow towards the center of the ffower; as the flower remains on the plant for several days, it loses almost all of the greenish-yellow leaving only a trace on the upper half of the throat of the flower; thus, the flower at its open and matured stage appears nearly pure white.
*Texture.*—Smooth.
Appearance: When the plant has just begun to bloom, the white flowers and nearly opened buds show the yellowish-green quite prominently; after the flowers have been open for several days, the greenish-yellow fades, becoming almost pure white. The anthers of the stamens are quite prominent. Flowers open very wide becoming almost flat across the flowers; however, there is depth in the throat making it a trumpet-shaped flower.
Shape: Trumpet-shaped.
Arrangement: 3 on each stem; occasionally only 2, rarely 4.
Persistence: Sets buds regularly every year.

*Reproductive organs*

Stamens: Usually 6; occasionally 5 and rarely 4.
*Anther.*—Normal; light brown.
*Filament.*—White.
Pollen: Yellow.
Pistil: Normal.
*Style.*—White.
*Stigma.*—Ivory.
Ovary: Normal.

Having illustrated and described the invention or discovery, what is claimed as new and patentable is:

A distinct and new variety of white azalea plant, substantially as illustrated and described hereinabove, and characterized generally by its trumpet shaped hose-in-hose flower having prominent stamens, and particularly characterized by its exceptionally late blooming season from a heavy consistent set of greenish-yellow buds in which the greenish-yellow color decreases in saturation on the petals as the flower opens.

No references cited.